US00PP34756P2

(12) United States Plant Patent
Bisschop et al.

(10) Patent No.: US PP34,756 P2
(45) Date of Patent: Nov. 22, 2022

(54) LUPINE PLANT NAMED 'ET LPN 813'

(50) Latin Name: ***Lupinus* hybrid**
Varietal Denomination: ET LPN 813

(71) Applicants: Elisabeth Bisschop, Boijl (NL); Bart Noordhuis, Boijl (NL)

(72) Inventors: Elisabeth Bisschop, Boijl (NL); Bart Noordhuis, Boijl (NL)

(73) Assignee: ETERNAL PLANT BOIJL B.V., Boijl (NL)

( * ) Notice: Subject to any disclaimer, the term of this patent is extended or adjusted under 35 U.S.C. 154(b) by 29 days.

(21) Appl. No.: 17/672,548

(22) Filed: Feb. 15, 2022

(51) Int. Cl.
*A01H 5/02* (2018.01)
*A01H 6/54* (2018.01)

(52) U.S. Cl.
USPC ..... Plt./263.1

(58) Field of Classification Search
USPC ..... Plt./263.1
See application file for complete search history.

*Primary Examiner* — Karen M Redden
(74) *Attorney, Agent, or Firm* — C. Anne Whealy

(57) ABSTRACT

A new and distinct cultivar of Lupine plant named 'ET LPN 813', characterized by its upright and relatively compact plant habit; moderately vigorous growth habit and moderate growth rate; strong and sturdy flower stems; numerous large violet blue-colored flowers arranged on dense terminal racemes; and good garden performance.

1 Drawing Sheet

Botanical designation: *Lupinus* hybrid.
Cultivar denomination: 'ET LPN 813'.

CROSS-REFERENCED TO A RELATED APPLICATION & STATEMENT REGARDING PRIOR DISCLOSURES BY INVENTORS/APPLICANTS

This application claims priority to a European Community Plant Breeders' Rights application filed on Oct. 5, 2021, application number 2021/2498. There have been no offers for sale anywhere in the world prior to the effective filing date of this Application and no accessibility to one of ordinary skill in the art could have been derived from the printed Plant Breeder's Rights documents.

The Inventors/Applicants assert that no publications nor advertisements relating to sales, offers for sale or public distribution occurred more than one year prior to the effective filing date of this application. Any information about the claimed plant would have been obtained from a direct or indirect disclosure from the Inventors/Applicants. Inventors/Applicants claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of Lupine plant, botanically known as *Lupinus* hybrid and hereinafter referred to by the name 'ET LPN 813'.

The new Lupine plant is a product of a planned breeding program conducted by the Inventors in Boijl, The Netherlands. The objective of the breeding program is to develop new compact and freely flowering Lupine plants with a long flowering period.

The new Lupine plant originated from a cross-pollination in August, 2017 of a proprietary selection of *Lupinus* hybrid identified as code number EXC 25, not patented, as the female, or seed, parent with a proprietary selection of *Lupinus* hybrid identified as code number EBJH 67, not patented, as the male, or pollen, parent. The new Lupine plant was discovered and selected by the Inventor in July, 2018 as a single flowering plant within the progeny of the stated cross-pollination in a controlled environment in Boijl, The Netherlands.

Asexual reproduction of the new Lupine plant by in vitro meristem culture in a controlled greenhouse environment in Boijl, The Netherlands since August, 2018 has shown that the unique features of this new Lupine plant are stable and reproduced true to type in successive generations of asexual reproduction.

SUMMARY OF THE INVENTION

Plants of the new Lupine have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'ET LPN 813'. These characteristics in combination distinguish 'ET LPN 813' as a new and distinct Lupine plant:

1. Upright and relatively compact plant habit.
2. Moderately vigorous growth habit and moderate growth rate.
3. Strong and sturdy flower stems.
4. Numerous large violet blue-colored flowers arranged on dense terminal racemes.
5. Daylength neutral.
6. Good garden performance.

Plants of the new Lupine can be compared to plants of the female parent selection. Plants of the new Lupine differ primarily from plants of the female parent selection in the following characteristics:

1. Plants of the new Lupine are shorter than plants of the female parent selection.
2. Plants of the new Lupine are more freely flowering than plants of the female parent selection.

Plants of the new Lupine can be compared to plants of the male parent selection. Plants of the new Lupine differ primarily from plants of the male parent selection in the following characteristics:

1. Plants of the new Lupine are more compact and have shorter internodes than plants of the male parent selection.
2. Plants of the new Lupine have smaller leaves than plants of the male parent selection.
3. Plants of the new Lupine are daylength neutral whereas plants of the male parent selection are daylength dependent.

Plants of the new Lupine can be compared to plants of *Lupinus* hybrid 'ET LPN 802', disclosed in an U.S. Plant patent application Ser. No. 17/672,530. Plants of the new Lupine differ primarily from plants of 'ET LPN 802' in the following characteristics:

1. Plants of the new Lupine have slightly longer internodes than plants of 'ET LPN 802'.
2. Plants of the new Lupine have taller inflorescences than plants of 'ET LPN 802'.
3. Flowers of plants of the new Lupine are violet blue in color whereas flowers of plants of 'ET LPN 802' are light yellow in color.

BRIEF DESCRIPTION OF THE PHOTOGRAPH

The accompanying colored photograph illustrates the overall appearance of the new Lupine plant showing the colors as true as it is reasonably possible to obtain in colored reproductions of this type. Colors in the photograph may differ slightly from the color values cited in the detailed botanical description which accurately describe the colors of the new Lupine plant. The photograph is side perspective view of a typical flowering plant of 'ET LPN 813' grown in a container.

DETAILED BOTANICAL DESCRIPTION

The aforementioned photograph and following observations, measurements and values describe plants of the new Lupine grown during the spring and summer in 26-cm containers in an outdoor nursery in Boijl, The Netherlands and under cultural practices typical of commercial Lupine production. During the production of the plants, day temperatures ranged from 18° C. to 22° C. and night temperatures ranged from 10° C. to 16° C. Plants were one year old when the photograph and the detailed description were taken. In the detailed description, color references are made to The Royal Horticultural Society Colour Chart, 2001 Edition, except where general terms of ordinary dictionary significance are used.

Botanical classification: *Lupinus* hybrid 'ET LPN 813'.

Parentage:

*Female, or seed, parent*.—Proprietary selection of *Lupinus* hybrid identified as code number EXC 25, not patented.

*Male, or pollen, parent*.—Proprietary selection of *Lupinus* hybrid identified as code number EBJH 67, not patented.

Propagation:

*Type*.—By in vitro meristem culture.

*Time to initiate roots, summer*.—About seven to eight days at ambient temperatures about 20° C. and substrate temperatures about 15° C.

*Time to produce a rooted young plant, summer*.—About four to six weeks at ambient temperatures about 20° C. and substrate temperatures about 15° C.

*Root description*.—Medium in thickness, fleshy; typically close to 162C in color, actual color of the roots is dependent on substrate composition, water quality, fertilizer type and formulation.

*Rooting habit*.—Freely branching; medium in density.

Plant description:

*Plant and growth habit*.—Upright and relatively compact plant habit; moderately vigorous growth habit and moderate growth rate.

*Branching habit*.—Freely basal branching habit.

*Plant height, soil level to top of foliar plane*.—About 20 cm to 50 cm.

*Plant height, soil level to top of floral plane*.—About 75 cm to 105 cm.

*Plant diameter* (*area of spread*).—About 45 cm.

*Internode length*.—About 6 to 8 cm.

*Stem strength*.—Moderately strong to strong.

*Texture and luster*.—Pubescent; semi-glossy to matte.

*Color, developing and developed*.—Close to 145A.

Leaf description:

*Arrangement*.—Alternate and slightly whorled; palmately compound with about eight to twelve leaflets per leaf.

*Leaf length*.—About 8 cm to 15 cm.

*Leaf width*.—About 16 cm.

*Leaflet length*.—About 5 cm to 7 cm.

*Leaflet width*.—About 1 cm to 2 cm.

*Leaf shape*.—Palmate, roughly orbicular in outline.

*Leaflet shape*.—Lanceolate to oblanceolate.

*Leaflet apex*.—Acute to obtuse.

*Leaflet base*.—Cuneate.

*Leaflet margin*.—Entire.

*Leaflet texture and luster, upper surface*.—Smooth, glabrous; matte.

*Leaflet texture and luster, lower surface*.—Pubescent, rugose; matte.

*Leaflet venation pattern*.—Pinnate.

*Leaflet color*.—Developing leaflets, upper surface: Close to 143A. Developing leaflets, lower surface: Close to 147B. Fully expanded leaflets, upper surface: Darker than 143A; venation, close to 144B. Fully expanded leaflets, lower surface: Close to 147B; venation, close to 144C to 144D.

*Leaf petioles*.—Length: About 12 cm to 20 cm. Diameter: About 2 mm to 4 mm. Texture and luster, upper and lower surfaces: Smooth to pubescent; semi-glossy to matte. Strength: Moderately strong to strong. Color, upper and lower surfaces: Close to 145A.

*Stipules*.—Quantity and arrangement: One or two at the base of the petiole. Length: About 1.5 cm to 2 cm. Width: About 3 mm to 6 mm. Shape: Lanceolate. Color, upper and lower surfaces: Close to 143A.

Flower description:

*Flower appearance and arrangement*.—Large single papilionaceous flowers arranged in dense terminal racemes; freely flowering habit with usually about 100 flowers developing per inflorescence and up to 1,000 flowers developing per plant during the flowering season; flowers face initially erect to mostly outwardly with development.

*Natural flowering season*.—Continuous flowering from spring into the summer in The Netherlands.

*Flower longevity*.—Flowers last about two to three weeks on the plant; flowers not persistent.

*Fragrance*.—Moderately fragrant; peppery.

*Inflorescence height*.—About 50 cm.

*Inflorescence diameter*.—About 6 cm to 10 cm.

*Flower diameter*.—About 2 cm to 4 cm.

*Flower length* (*height*).—About 2.5 cm.

*Flower buds*.—Length: About 1 cm to 3 cm. Diameter: About 1 cm. Shape: Ovate. Texture and luster: Smooth, glabrous; semi-glossy to matte. Color: Close to 145A becoming closer to 86B with development.

*Petals*.—Quantity per flower: Flowers papilionaceous with an upper (standard) petal, two lateral (wing) petals and a lower (keel) petal; petals not fused. Length: Upper petal: About 2 cm. Lateral petals: About 2 cm. Lower petal: About 1 cm. Width: Upper petal: About 2 cm. Lateral petals: About 1 cm. Lower petal: About 5 mm. Shape: Upper petal: Orbicular. Lateral petals: Obovate. Lower petal: Ovate. Apex: Upper petal: Rounded. Lateral petals: Obtuse. Lower petal: Caudate. Base, all petals: Cordate. Margin, all petals: Entire; not undulate. Texture and luster, upper and lower surfaces, all petals: Smooth, glabrous; satiny; matte. Color, when opening, upper surface: Upper petal: Close to 94A flushed with close to N81B. Lateral petals: Close to 94D. Lower petal: Close to 94D; apex, close to 94A. Color, when opening, lower surface: Upper petal: Close to 94B. Lateral petals: Close to 94C. Lower petal: Close to 94D. Color, fully opened, upper surface: Upper petal: Close to 94A flushed with close to N81B; color does not change with subsequent development. Lateral petals: Close to 94D; towards the margins, close to N81B; color does not change with subsequent development. Lower petal: Close to 94D; apex, close to 94A; color does not change with subsequent development. Venation, all petals: Close to lamina colors or close to 94A. Color, fully opened, lower surface: Upper petal: Close to 94B; color does not change with subsequent development. Lateral petals: Close to 94C; color does not change with subsequent development. Lower petal: Close to 94D; color does not change with subsequent development. Venation, all petals: Close to lamina colors or close to 94A.

*Sepals*.—Quantity per flower and arrangement: Two, opposite. Length: About 3 mm to 5 mm. Width: About 2 mm to 3 mm. Shape: Ovate. Apex: Acute. Base: Obtuse to cordate. Margin: Entire. Texture and luster, upper and lower surfaces: Smooth, glabrous; satiny; slightly glossy to matte. Color: When opening and fully opened, upper surface: Close to 145C. When opening and fully opened, lower surface: Close to 145C.

*Peduncles*.—Length: About 75 cm to 110 cm. Diameter: About 1 cm to 3 cm. Strength: Strong and sturdy. Aspect: Mostly erect. Texture and luster: Smooth, glabrous; matte. Color: Close to 144C to 144D.

*Pedicels*.—Length: About 5 mm to 7 mm. Diameter: About 2 mm. Strength: Moderately strong. Aspect: About 70° to 80° from peduncle axis Texture and luster: Smooth, glabrous; matte. Color: Close to 145B.

*Reproductive organs*.—Androecium: Quantity per flower: About six to nine. Filament length: About 7 mm to 9 mm. Filament color: Close to 145D. Anther length: About 1 mm to 3 mm. Anther shape: Oblong. Anther color: Close to 21A. Amount of pollen: Abundant. Pollen color: Close to 21A. Gynoecium: Quantity per flower: One. Pistil length: About 1 cm. Style length: About 5 mm to 8 mm. Style color: Whiter than 145D. Stigma diameter: About 1 mm. Stigma shaped: Rounded. Stigma color: Whiter than 145D. Ovary color: Close to 143D.

*Fruits and seeds*.—To date, fruit and seed development has not been observed on plants of the new Lupine.

Garden performance: In the garden, plants of the new Lupine have been observed to be daylength neutral. Additionally, plants of the new Lupine have been observed to have good garden performance and to tolerate rain, wind, temperatures ranging from about −20° C. to about 40° C.

Pathogen & pest resistance: To date, plants of the new Lupine have not been observed to be resistant to pathogens and pests common to Lupine plants.

It is claimed:

1. A new and distinct Lupine plant named 'ET LPN 813' as illustrated and described.

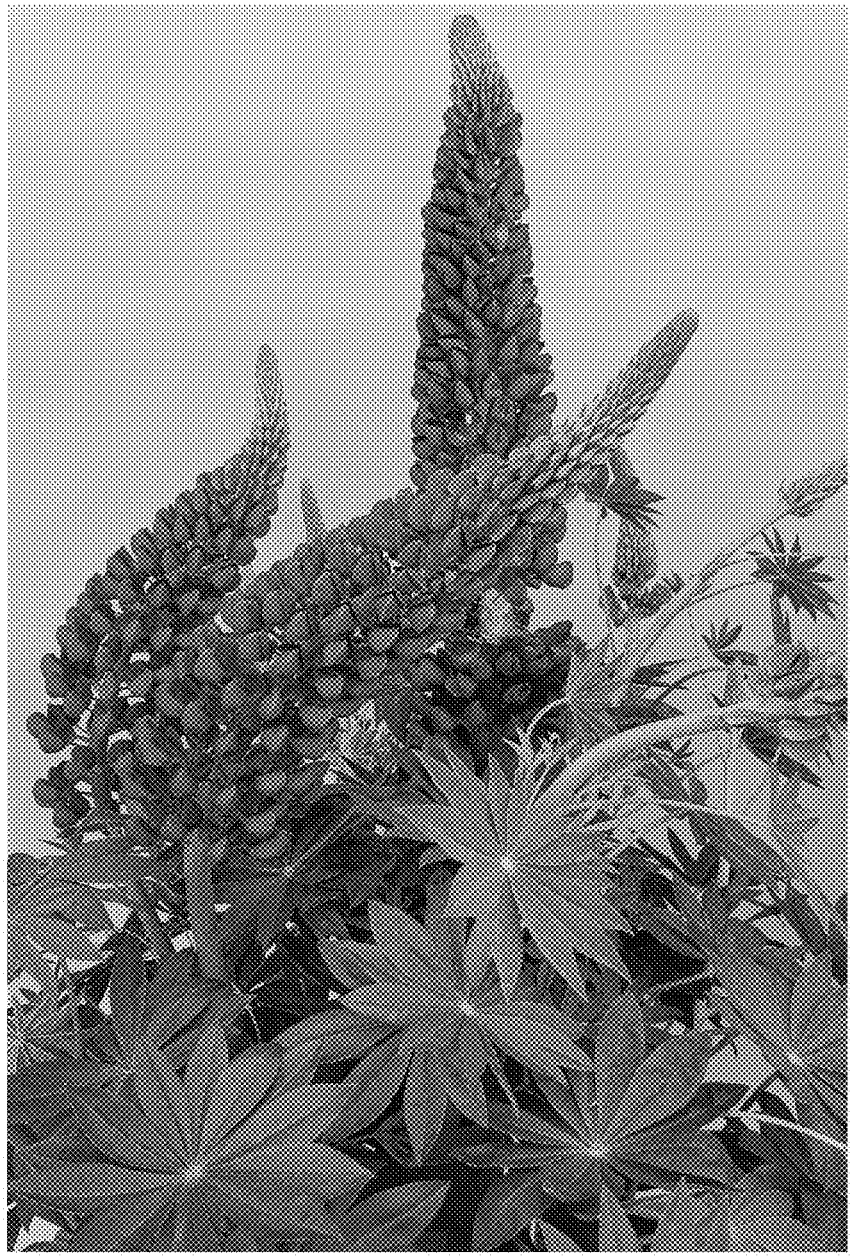

* * * * *